United States Patent [19]

Yamazaki

[11] Patent Number: 4,617,059
[45] Date of Patent: Oct. 14, 1986

[54] DEMOLITION AGENT FOR BRITTLE MATERIALS

[75] Inventor: Yukinori Yamazaki, Tokyo, Japan

[73] Assignee: Nihon Cement Co., Ltd., Tokyo, Japan

[21] Appl. No.: 722,197

[22] Filed: Apr. 11, 1985

Related U.S. Application Data

[63] Continuation of Ser. No. 556,032, Nov. 29, 1983, abandoned.

[51] Int. Cl.$^4$ .............................................. B02C 19/00
[52] U.S. Cl. ...................................... 106/118; 106/89; 423/175; 423/304; 423/637
[58] Field of Search ............... 106/109, 110, 117, 118, 106/119, 89, 90; 423/175, 178, 636, 639

[56] References Cited

U.S. PATENT DOCUMENTS

| 3,679,363 | 7/1972 | Skrivan | 423/323 |
| 3,884,710 | 5/1975 | Allen et al. | 106/89 |
| 4,162,170 | 7/1979 | Grancharove et al. | 423/555 |
| 4,316,583 | 2/1982 | Kawano et al. | 106/90 |
| 4,378,997 | 4/1983 | Kasama et al. | 106/89 |
| 4,508,574 | 4/1985 | Kurand et al. | 106/121 |

FOREIGN PATENT DOCUMENTS

| 520829 | 5/1940 | United Kingdom | 423/637 |
| 629179 | 9/1978 | U.S.S.R. | 106/109 |
| 682467 | 9/1979 | U.S.S.R. | 423/638 |

*Primary Examiner*—Andrew H. Metz
*Assistant Examiner*—McFarlane Anthony
*Attorney, Agent, or Firm*—Wyatt, Gerber, Shoup, Scobey and Badie

[57] ABSTRACT

A demolition agent for brittle materials which is prepared by pulverizing a quick lime clinker including 0.5 to 10.0% by weight of phosphorus components in terms of $P_2O_5$.

2 Claims, No Drawings

DEMOLITION AGENT FOR BRITTLE MATERIALS

This application is a continuation of U.S. application Ser. No. 556,032, filed 11/29/83, now abandoned.

The present invention relates to a demolition agent for brittle materials such as rock, concrete and the like.

A quick lime can be obtained generally by calcining a limestone in a vertical kiln, a rotary kiln or the like, but the hydration rate of the quick lime varies with calcination temperature, calcination time, etc. When used as a demolition agent, a quick lime is selected in which the hydration rate, this is the activity, is as low as possible. For the preparation of low-activity quick lime, it is necessary to increase the calcination temperature and to lengthen the calcination time of the limestone. For this reason, the operation of the kiln and the preparation of a uniform calcined product are difficult, and a greater amount of energy is required. A method for preparing the low-activity quick lime at a low calcination temperature comprises calcining a material in which the purity of the limestone is poor or in which impurities such as silica, alumina and iron oxide are mixed with the limestone, but when the method is used, the purity of the limestone is degraded, and the impurities will react with a large amount of limestone, which will disadvantageously lead to the reduction in the amount of the substantially effective quick lime and thus the deterioration in its demolition power.

An object of the present invention is to provide a demolition agent for brittle materials while avoiding the aforesaid drawbacks.

According to the present invention, there is provided a demolition agent for brittle materials which is prepared by pulverizing a quick lime clinker including 0.5 to 10.0% by weight of phosphorus components in terms of $P_2O_5$.

The present invention has been achieved on the basis of the discovery that the incorporation of phosphorus components into quick lime permits the calcination temperature of the quick lime to drop, thereby obtaining a low-activity quick lime particularly without requiring calcination conditions at a high temperature for a long period of time. The effects of the phosphorus components would be presumed to be due to the phenomenon that the phosphorus components react with silica, alumina and iron present in the limestone during the calcination process in order to produce a liquid phase at a lower temperature than the calcination temperature at the time of the usual manufacture of the low-activity quick lime and that the phosphorus components is dissolved in the quick lime to produce a solid solution.

Phosphorus can be present in various forms in caustic lime. Although it is present in the form of phosphate (e.g. $Ca_3(PO_4)_2$, $Ca(H_2PO_4).H_2O$, $NaH_2PO_4$, $Na_2HPO_4$, $Na_3PO_4$), other forms (e.g. $Ca_5(F, Cl)(PO_4)_3$), $P_2O_5$ are also useful. With respect to the content of phosphorus, in the case of conversion to the form of $P_2O_5$, 0.5–10.0% by weight is desirable.

When the phosphorus content in the quick lime is less than 0.5% by weight in terms of $P_2O_5$, a lesser effect will be expected in calcining the quick lime, so that the low-activity quick lime will scarcely be obtained. On the contrary, when the phosphorus content is more than 10% by weight in terms of $P_2O_5$, amount of the effective quick lime will decrease and the demolition power will be weakened. Therefore, it is preferred that the phosphorus content is from 0.5 to 7.0% by weight in terms of $P_2O_5$.

In order to cause the phosphorus components to be present in the quick lime, the limestone including the phosphorus components may be calcined. Alternatively a method may be used in which a phosphorus compound, rock phosphate, phosphorus-including waste or the like is mixed with the limestone prior to calcination.

In this case, miscellaneous components which may be present in the quick lime clinker are up to 4% $SiO_2$, up to 2% $Al_2O_3$ and up to 2% $Fe_2O_3$, and the effective quick lime is preferably present in large quantities.

Effects of the present invention are as follows: In preparing the low-activity quick lime effective as a demolition agent for brittle materials, the calcination temperature of the quick lime can be lower than the conventionally employed temperature, i.e. 1600° C. or more, by approximately 150° C., which will lead to the saving of the fuel. Further, since the calcination at an unreasonably high temperature is not required, operation is stable and the preparation of quick lime of poor quality is prevented. Furthermore, since the effective quick lime is present in large quantities in the demolition agent for brittle materials, and since the low-activity quick lime is included therein, a prolonged casting time (workable time) can be obtained, and a high expansion pressure will generate, so that great demolition power can be obtained.

EXPERIMENTAL EXAMPLE

Calcium phosphate was mixed with a limestone having the chemical composition set forth in Table 1 below so that phosphorus contents in quick lime clinkers were 0.05, 0.5, 1.0, 2.0 and 5% by weight in terms of $P_2O_5$. The resulting mixtures were each pulverized and formed into pellets, followed by a calcinating treatment at 1450° C. for one hour in an electric furnace in order to obtain a quick lime clinker. The thus obtained quick lime clinkers were each pulverized to a powder having a Blaine specific surface area of approximately 2,000 $cm^2/g$, and an activity test was carried out by the use of a Dewar's vessel.

The activity test was accomplished by placing 400 cc of water in the Dewar's vessel in a thermostatic chamber of 20° C., adding thereto 100 g of each powdery quick lime sample for 30 seconds with stirring, and measuring the temperature rise of the resulting slurry. Values of the aforesaid temperature rise were measured 10 minutes after mixing with water and were adopted as the activities of the quick lime samples.

the results are set forth in Table 2.

TABLE 1

| Chemical analysis of limestone (wt. %) | | | | | | | |
|---|---|---|---|---|---|---|---|
| Ig. loss | $SiO_2$ | $Al_2O_3$ | $Fe_2O_3$ | CaO | MgO | $P_2O_5$ | Total |
| 43.0 | 1.3 | 0.2 | 0.1 | 54.9 | 0.3 | 0.02 | 99.82 |

TABLE 2

| Phosphorus content in and activity of quick lime clinker | | |
|---|---|---|
| Sample No. | $P_2O_5$ Amount in quick lime clinker (wt %) | Activity (°C.) |
| 1 | 0.05 | 78 |
| 2 | 0.5 | 31 |
| 3 | 1.0 | 13 |
| 4 | 2.0 | 9 |

TABLE 2-continued

| | Phosphorus content in and activity of quick lime clinker | |
|---|---|---|
| Sample No. | P$_2$O$_5$ Amount in quick lime clinker (wt %) | Activity (°C.) |
| 5 | 5.0 | 7 |

As indicated by the results just described, the quick lime samples including 0.5% or more of the phosphorus components in terms of P$_2$O$_5$ were low-activity.

EXAMPLES 1 TO 3

Rock phosphate and ash obtained by incinerating sewage were added to the limestone having the composition set forth in Table 1 above, and the procedure of the above-mentioned Experimental Example was repeated to prepare powdery quick lime samples. Then, 80 wt. parts of each powdery quick lime were mixed with 20 wt. parts of a ordinary Portland cement to manufacture a demolition agent. the demolition power of the demolition agent was represented by the expansion pressure generated at the time when the sample of the demolition agent was charged in a steel pipe. The measurement of the expansion pressure was carried out as follows: To 100 wt. parts of the demolition agent, 30 wt. parts of water were added in order to prepare a slurry; the prepared slurry was injected into a steel pipe (inner diameter 38.4 mm, outer diameter 48.6 mm and length 1000 mm) having a bottom plate; detecting an expansion ratio of the steel pipe resulting from the hydration of the quick lime by means of a strain gauge; and calculating the expansion pressure on the basis of a formula for stress and strain in pressure vessel, i.e. a thick cylinetrical steel pipe.

Further, the amount of the effective quick lime was represented with the amount of free lime which could be measured by a glycerin-alcohol method.

Results of the tests are set forth in Table 3 below.

TABLE 3

Chemical analysis, activity and effective quick lime amount of quick lime, and expansion pressure of demolition agent

| | Phosphorus material and amount (based on quick lime) | | Chemical analysis (%) | | | | | Effective quick lime amount | Activity (°C.) | Expansion pressure (Kgf/cm$^2$) |
|---|---|---|---|---|---|---|---|---|---|---|
| | | | SiO$_2$ | Al$_2$O$_3$ | Fe$_2$O$_3$ | CaO | P$_2$O$_5$ | | | |
| Comparative Example 1 | | 0 | 2.2 | 0.3 | 0.2 | 96.3 | 0.03 | 88.5 | 78 | Unmeasured |
| Example 1 | Rock phosphate | 3% | 2.4 | 0.3 | 0.2 | 94.8 | 1.1 | 87.5 | 10 | 387 |
| Example 2 | Rock phosphate | 15 | 3.0 | 0.4 | 0.2 | 89.3 | 4.9 | 75.0 | 6 | 311 |
| Example 3 | Rock phosphate | 20 | 3.4 | 0.4 | 0.3 | 86.1 | 6.5 | 70.7 | 5 | 253 |
| Example 4 | Sludge ash | 10 | 3.9 | 1.0 | 1.5 | 91.0 | 0.6 | 76.1 | 7 | 335 |

Note:
The above-mentioned unmeasurableness of the expansion pressure means that because of a high activity, the slurry could not be prepared, so that the sample could not be injected into the steel pipe.

Table 3 indicates that quick limes including 0.5% or more phosphorus components in terms of P$_2$O$_5$ have low activities, and the demolition agents comprising these quick limes have high expansion pressures, i.e. great demolition powers.

What is claimed is:

1. A demolition agent for brittle materials which is prepared by pulverizing a mixture containing limestone and phosphorus components together with SiO$_2$, Al$_2$O$_3$ and Fe$_2$O$_3$, calcining said mixture, and pulverizing resulting quick lime clinker, said demolition agent consisting of 0.5 to 10% by weight of phosphorous components in terms of P$_2$O$_5$, up to 4% SiO$_2$, up to 2% Al$_2$O$_3$, up to 2% Fe$_2$O$_3$, balance lime.

2. A demolition agent as in claim 1 wherein the percent by weight of phosphorous components in terms of P$_2$O$_5$ is 0.5 to 7%.

* * * * *

UNITED STATES PATENT AND TRADEMARK OFFICE
CERTIFICATE OF CORRECTION

PATENT NO. : 4,617,059
DATED : October 14, 1986
INVENTOR(S) : Yukinori Yamazaki

It is certified that error appears in the above—identified patent and that said Letters Patent is hereby corrected as shown below:

Column 1, line [63] change "556,032" to read --556,031--

Signed and Sealed this

Third Day of March, 1987

Attest:

DONALD J. QUIGG

*Attesting Officer*    *Commissioner of Patents and Trademarks*